(12) United States Patent
Teles et al.

(10) Patent No.: US 8,492,584 B2
(45) Date of Patent: Jul. 23, 2013

(54) PROCESS AND APPARATUS FOR OXIDIZING ORGANIC COMPOUNDS

(75) Inventors: Joaquim Henrique Teles, Otterstadt (DE); Steffen Oehlenschläger, Ludwigshafen (DE); Kai Gumlich, Mannheim (DE); Martin Schäfer, Grünstadt (DE); Stephan Lamm, Oftersheim (DE); Stefan Berg, Frankenthal (DE); Michael Nilles, Bobenheim-Roxheim (DE); Hans-Peter Schildberg, Neustadt (DE); Tilo John, Speyer (DE); Peter Zehner, Weisenheim Am Berg (DE)

(73) Assignee: BASF SE, Ludwigshafen (DE)

( * ) Notice: Subject to any disclaimer, the term of this patent is extended or adjusted under 35 U.S.C. 154(b) by 408 days.

(21) Appl. No.: 12/674,466

(22) PCT Filed: Aug. 18, 2008

(86) PCT No.: PCT/EP2008/060786
§ 371 (c)(1),
(2), (4) Date: Feb. 22, 2010

(87) PCT Pub. No.: WO2009/024549
PCT Pub. Date: Feb. 26, 2009

(65) Prior Publication Data
US 2011/0137077 A1   Jun. 9, 2011

(30) Foreign Application Priority Data
Aug. 21, 2007   (EP) .................................... 07114708

(51) Int. Cl.
*C07C 51/215*   (2006.01)
(52) U.S. Cl.
USPC .......................... 562/533; 562/531; 562/532

(58) Field of Classification Search
USPC .......................................... 562/531, 532, 533
See application file for complete search history.

(56) References Cited

U.S. PATENT DOCUMENTS

| | | |
|---|---|---|
| 4,900,480 A | 2/1990 | Litz et al. |
| 6,479,680 B1 | 11/2002 | Bassler et al. |
| 6,696,582 B2 | 2/2004 | Springer et al. |
| 6,838,061 B1 | 1/2005 | Berg et al. |
| 2006/0047147 A1 | 3/2006 | Wonders et al. |

FOREIGN PATENT DOCUMENTS

| | | |
|---|---|---|
| CN | 1569798 A | 1/2005 |
| DE | 19835907 A1 | 2/2000 |
| DE | 19854637 A1 | 5/2000 |
| EP | 0439013 A1 | 7/1991 |
| EP | 0792865 A1 | 9/1997 |
| WO | WO-99/54274 A1 | 10/1999 |
| WO | WO-00/30743 A1 | 6/2000 |
| WO | WO-01/46111 A1 | 6/2001 |
| WO | WO-01/66505 A1 | 9/2001 |

OTHER PUBLICATIONS

U.S. Appl. No. 12/674,058, filed Feb. 18, 2010.

*Primary Examiner* — Taylor Victor Oh
(74) *Attorney, Agent, or Firm* — Novak Druce Connolly Bove + Quigg LLP

(57) ABSTRACT

The invention relates to a process for oxidizing at least one organic substance with oxygen, which comprises the following steps:
(a) adding the at least one organic substance as a liquid and an oxygenous gas stream to a first reaction stage to form a reaction mixture, at least some of the oxygen reacting with the organic compound to form a reaction product,
(b) adding the reaction mixture from the first reaction stage to an adiabatically operated reaction stage in which the unconverted organic substance reacts further at least partly to give the product.

Figure 1:
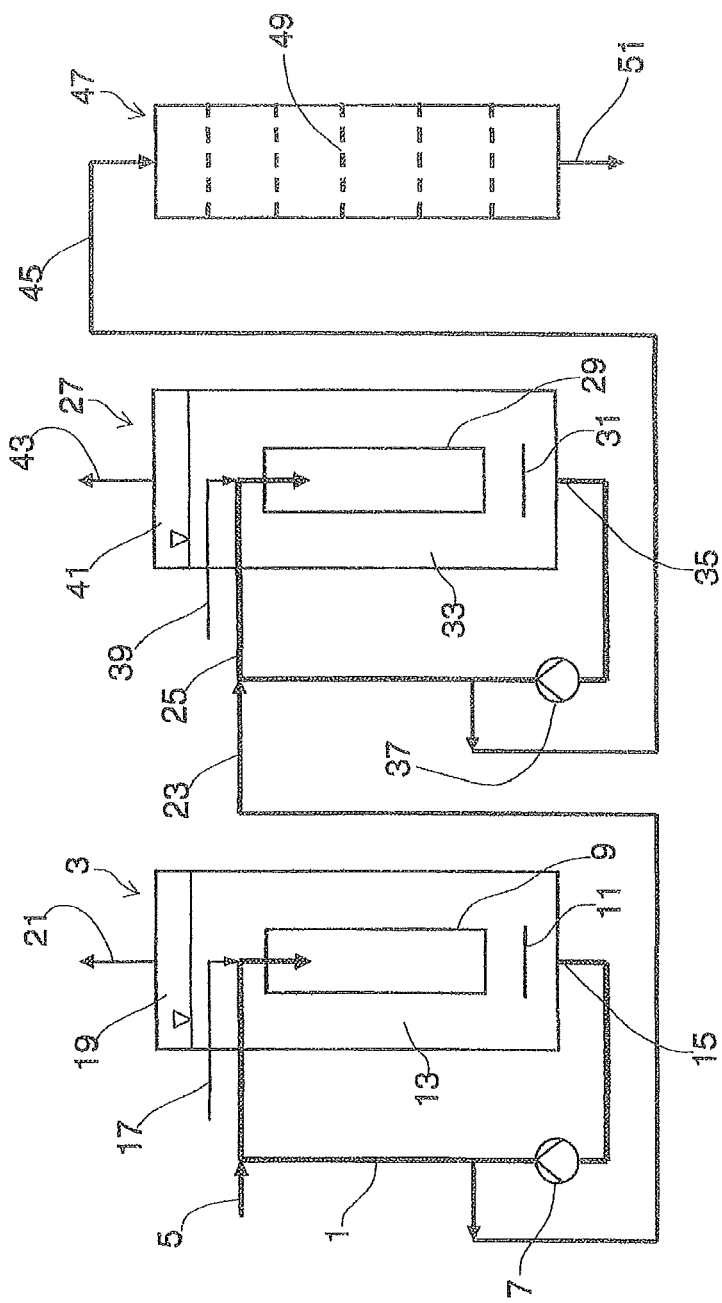

The invention further relates to an apparatus for performing the process.

20 Claims, 3 Drawing Sheets

PROCESS AND APPARATUS FOR OXIDIZING ORGANIC COMPOUNDS

RELATED APPLICATIONS

This application is a national stage application (under 35 U.S.C. §371) of PCT/EP2008/060786, filed Aug. 18, 2008, which claims benefit of European application 07114708.6, filed Aug. 21, 2007.

The invention relates to a process for oxidizing organic compounds with oxygen. The invention further relates to an apparatus for performing the process.

The process is suitable, for example, for oxidizing aldehydes with an oxygenous gas to their corresponding acids.

The preparation of organic acids is known, for example, from WO 99/54274. For this purpose, one or more organic liquids are oxidized with essentially pure oxygen or oxygen-enriched air which comprises at least 50% oxygen in a liquid oxidation reactor. The temperature is kept within a range of ±3° C. around a target temperature. After the reaction, the reaction mixture is worked up. The workup is effected, for example, by distillation, solvent extraction, crystallization, evaporation, phase separation, filtration or the like. For the reaction, a loop reactor in which a guide tube is present in the reactor is used. In the space between the guide tube and the outer wall of the reactor, a heat exchanger is accommodated. By means of a stirrer in the guide tube, the liquid flow in the reactor is generated. A disadvantage of the process described here is that, although the conversion can be enhanced to up to 98% by means of a second reactor which is connected in series with the first reactor, the reaction rate is so low that a third stage to further increase the conversion is economically unviable.

A loop reactor for performing gas-liquid, liquid-liquid or gas-liquid-solid reactions is known from WO-A 00/30743. The reactor comprises a jet nozzle which points downward, is arranged in the upper reactor region and through which the reactants and the reaction mixture are supplied, and an outlet, preferably in the lower reactor region, through which the reaction mixture is sent back to the jet nozzle in an outer circuit by means of a pump. In the reactor is arranged a concentric guide tube which extends essentially over the entire length of the reactor with the exception of the reactor ends. The guide tube has a cross-sectional area in the range from $\frac{1}{10}$ up to half of the cross-sectional area of the reactor. The jet nozzle is arranged above the upper end of the guide tube, preferably spaced apart from it by from $\frac{1}{8}$ of the guide tube diameter up to one guide tube diameter, or is immersed into the guide tube in a depth up to several guide tube diameters. A heat exchanger is integrated into the ring space. The reactor is used, for example, to prepare propionic acid from propionaldehyde. To this end, the propionaldehyde is oxidized with air. In order to achieve an increased conversion, it is stated that a plurality of the reactors are connected in series. A disadvantage of the process described here is that, even in the case of series connection of two reactors, virtually complete conversion of the aldehyde is not achieved. Although it would be conceivable to use a third reactor in order to achieve the desired high conversion, such a procedure would be economically unviable as a result of the complexity of this reactor type and the associated high capital costs.

WO 01/66505 discloses a process for preparing aliphatic carboxylic acids having from 4 to 10 carbon atoms by oxidizing the corresponding aldehydes with oxygen or oxygen-comprising gases. The oxidation is performed within the temperature range from 0 to 100° C. in at least two stages at temperatures rising from stage to stage. The temperature is raised in each case by at least 5° C. One reactor is provided for each reaction stage. The reactors described are, for example, tubular reactors which, if appropriate, also comprise random packings, trickle towers which comprise random packings, or bubble columns. However, a disadvantage of this process is that the majority of the heat of reaction has to be removed at a low temperature of below 50° C. Moreover, complete conversions cannot be achieved within acceptable reaction times with this process. For example, as is evident from example 1 of WO 01/66505, a conversion of 98.2% is not achieved until after 6 hours.

WO 01/46111 also discloses a process for oxidizing an organic substance, in which air, oxygen, oxygen-enriched or oxygen-comprising air is passed into a liquid in a reaction system. The reaction is performed at a temperature in the range between 20 and 100° C. and a pressure in the range between 0 and 3 bar. In the reaction system, means of achieving mixing of the amount of liquid are provided. To achieve mixing, for example, it is possible to use stirrers, axial impellers, turbines, injectors, submerged porous diffusers, spargers or surface aerators. Baffles may be accommodated in the reactor. However, a disadvantage of the process described here is also that a virtually full conversion cannot be achieved.

The oxidation of aldehydes with pure oxygen or a gas which comprises at least 50% oxygen is described in EP-A 0 792 865. The reaction is performed in a reactor as described in U.S. Pat. No. 4,900,480. This specific reactor can achieve relatively high conversions, but at the cost of a significantly more complex reactor. Owing to the need to dilute the headspace with inert gas, these reactors, in spite of the use of pure oxygen, still have significant amounts of offgas which has to be treated. A similar approach to the oxidation of organic chemicals is also described in EP-A 0 439 013.

A process for oxidizing propionaldehyde to propionic acid using a bubble column or a stirred tank reactor is described in CN-A 1569798. The process achieves high conversions of approx. 99% and selectivities in the range from 97.2 to 98%, but this is achieved, in spite of the use of pure oxygen as an oxidizing agent, as evident from example 1 of CN-A 1569798, with an only moderate space-time yield of 75 g/l h. The use of pure oxygen additionally leads to considerable safety problems at the reactor outlet when a coherent gas phase forms, which will then be ignitable.

It is an object of the present invention to provide a process for oxidizing organic substances which has a simple reactor design and enables high space-time yields. In addition, a substantially full conversion of the organic substance shall be achieved in order to make the downstream workup as simple as possible. For example, this makes it possible to dispense with recycling of unconverted reactant into the reaction stage. It is a further object of the invention to provide an apparatus for performing the process.

The object is achieved by a process for oxidizing at least one organic substance with oxygen, which comprises the following steps:

(a) adding the at least one organic substance as a liquid and an oxygenous gas stream to a first reaction stage to form a reaction mixture, at least some of the oxygen reacting with the organic compound to form a reaction product, (b) adding the reaction mixture from the first reaction stage to an adiabatically operated reaction stage in which the unconverted organic substance reacts further at least partly to give the product.

The process according to the invention is suitable, for example, for oxidizing hydrocarbons, olefins, phenols and aldehydes with an oxygenous mixture. Oxidations of hydrocarbons are, for example, the oxidation of cyclohexane to a mixture comprising cyclohexyl hydroperoxide, cyclohexanone, cyclohexanol and adipic acid, of isobutane to a mixture comprising tert-butyl hydroperoxide and tert-butanol, of isopentane to a mixture comprising tert-amyl hydroperoxide and tert-amyl alcohol, of ethylbenzene to a mixture comprising ethylbenzene hydroperoxide, 1-phenylethanol and acetophenone, of cumene to a mixture comprising cumene hydroperoxide and 2-phenyl-2-propanol, and of p-cymene to a mixture comprising p-cymene hydroperoxide and 2-(4-tolyl)-2-propanol. Oxidations of olefins are, for example, the oxidation of cyclopentene to a mixture comprising cyclopent-2-en-1-yl hydroperoxide, cyclopent-2-enol and cyclopent-2-enone, of 2,3-dimethylbutene-2 to a mixture comprising tetramethyloxirane. Oxidations of phenols are, for example, the oxidation of 2,3,6-trimethylphenol to a mixture comprising trimethylbenzoquinone, of 2,3,5-trimethylphenol to a mixture comprising trimethylbenzoquinone, of mesitol to a mixture comprising 2,4,6-trimethyl-4-hydroperoxycyclohexa-2,5-dien-1-one.

In particular, the process is suitable, however, for oxidizing aliphatic aldehydes with oxygen to form carboxylic acids. The aldehyde which is oxidized to its corresponding acid is preferably an aldehyde having from 3 to 18 carbon atoms. The aldehyde may be branched or unbranched. The aldehyde may also comprise ring structures. The aldehyde is more preferably saturated. Suitable aldehydes which can be used as reactants for the reaction are, for example, propanal, butanal, 2-methylpropanal, pentanal, 2-methylbutanal, 3-methylbutanal, 2,2-dimethylpropanal, hexanal, 2-methylpentanal, 3-methylpentanal, 2-ethylbutanal, heptanal, 2-methylhexanal, 2-ethylpentanal, octanal, 2-ethylhexanal, nonanal, decanal, 3,7-dimethyloctanal, 3,5,5-trimethylhexanal, cyclopentanecarbaldehyde, cyclohexanecarbaldehyde or a mixture of at least two of the aforementioned aldehydes.

The advantage of the process according to the invention in the oxidation of an aldehyde with oxygen is that the aldehyde is converted essentially fully. Essentially fully means that the conversion is greater than 98%, preferably greater than 99%.

When aldehyde mixtures are used as the organic substance, they are obtained, for example, in the hydroformylation of olefins or in the aldol condensation and partial hydrogenation of other aldehydes.

In a preferred embodiment, the reaction mixture from the first reaction stage, before being added to the adiabatically operated reaction stage, is sent to at least one further reaction stage. This means that the oxidation is performed in a battery of at least three reactors. As a result of the use of the at least one further reaction stage which is connected downstream of the first reaction stage and upstream of the adiabatically operated reaction stage, the reaction conversion can be increased further. To perform the reaction, the reaction mixture passes through the individual reaction stages successively. All reaction stages apart from the adiabatically operated reaction stage are preferably backmixed. The backmixing achieves a substantially homogeneous concentration distribution within the particular reaction stage. Furthermore, the heat of reaction can be removed in a technically simple manner.

The first reaction stage and, if appropriate, the at least one further reaction stage, i.e. all reaction stages apart from the adiabatically operated reaction stage, are preferably operated essentially isothermally. In the context of the present invention, operated essentially isothermally means that the temperature differences within one reaction stage are not greater than 10° C. This temperature difference arises essentially from the fluid dynamics of the particular reactor and the type of heat removal. When the heat, for example, is removed directly in the reaction chamber, it is possible to achieve a more uniform temperature profile than in the case of heat removal by means of an external-flow heat exchanger.

In one embodiment, the first reaction stage and the at least one further reaction stage are operated at essentially the same temperature. This means that the temperature differences between the mean temperatures of the individual reaction stages are not greater than 5° C.

However, it is preferably also possible that the first reaction stage and the at least one further reaction stage are operated such that the temperature increases from reaction stage to reaction stage. The temperature difference between the individual reaction stages is then preferably at least 5° C., more preferably at least 10° C.

The temperature at which the first reaction stage and, if appropriate, the at least one further reaction stage are operated is preferably in the range between 0 and 150° C., more preferably between 30 and 125° C. In order, however, to ensure a sufficiently high space-time yield and simultaneously to be able to remove the heat of reaction efficiently, a reaction temperature of at least 50° C. is preferred. More preferably, a reaction temperature of at least 60° C. is established. Especially preferably, the reaction temperature is at least 70° C.

The reaction pressure is preferably selected such that the partial pressure of the oxygen in the oxygenous gas stream supplied is in the range between 0.1 and 20 bar. The partial pressure of the oxygen is preferably within the range between 1 and 6 bar.

To perform the reaction, it is possible firstly that all of the oxygen required for the reaction is supplied to the first reaction stage. In this case, a mixture of the organic substance to be oxidized and the oxygenous gas is sent to the further reaction stages. In a preferred embodiment, however, oxygenous gas is also supplied to the at least one further reaction stage. In this case, it is preferred when a gas phase is removed from the reaction mixture in the reactors of the individual reaction stages. This gas phase is removed as offgas from the reactors. The offgas comprises unconverted oxygen and gas constituents which are present in the gas stream and are not required for the reaction. These gas constituents are preferably inert in relation to the oxidation performed. Corresponding gas constituents are, for example, nitrogen or carbon dioxide. In addition, the offgas generally also comprises gaseous reactant and gaseous product.

The adiabatic reaction stage can be operated in monophasic liquid or sparged form. In a preferred embodiment of the process according to the invention, oxygenous gas is also supplied to the adiabatically operated reaction stage. In this way, it is ensured that an oxidation of the organic substance also proceeds in the adiabatically operated reaction zone, which further increases the reaction conversion.

In a preferred embodiment, the oxygenous gas which is supplied to the adiabatically operated reaction stage is the offgas of at least one of the preceding reaction stages. This is preferred especially when as yet unconverted oxygen is present in the offgas of the preceding reaction stages. Since the reaction stages are generally operated with an oxygen excess, oxygen is generally still present in the offgas of the individual reaction stages. The advantage of the embodiment in which offgas of at least one of the preceding reaction stages is supplied to the adiabatically operated reaction stage is that this minimizes the amount of offgas.

The oxygenous gas used, which is supplied to the reaction, is preferably a gas mixture which comprises not more than 50% by volume of oxygen. Very particular preference is given to the use of air. The advantage of using air is that safe operation of the reaction stages can be achieved, since the reactor can then be operated in such a way that the proportion of oxygen in the offgas is below the amount at which an ignitable mixture is present. The amount of oxygenous gas for each individual reaction stage is preferably selected such that the concentration of oxygen in the offgas is less than 10% by volume, more preferably less than 8% by volume. At these concentrations, the offgas is not ignitable. In this way, safety problems are avoided, and the addition of expensive nitrogen to inertize the gas chamber is not required.

In order to prevent substances of value from being lost through the offgas, it is preferred when product and reactant present in the offgas of the individual reaction stages is removed therefrom. The reactant can subsequently be fed back to the reaction. For this purpose, preference is given to collecting the offgas from the individual reaction stages and sending it to a purification in which reactant and product are removed from the offgas. The removal is effected preferably by scrubbing in a scrubbing column. After the removal of reactants and products, it is preferred when the reactant is removed and sent back to the reaction. In a particularly preferred embodiment, the offgas is contacted in a scrubbing column with the effluent of the adiabatically operated reaction stage as the scrubbing substance. The laden scrubbing substance is then recycled into one of the isothermally operated reaction stages. In order to prevent substances which are harmful to the environment and may be present in the offgas from being released to the environment, it is preferred when the offgas is disposed of by means of a flare. For the scrubbing, it is possible to use any desired scrubbing column known to those skilled in the art. Suitable scrubbing substances are, for example, water, organic solvent used in the process, reactant or reactant mixture, product or product mixture. Particular preference is given to using, as the scrubbing, liquid, the product or product mixture which is being produced in the plant at the time. Very particular preference is given to using, as the scrubbing substance, the liquid product from the adiabatically operated reaction stage. In a particularly preferred embodiment, the scrubbing substance used is cooled before use to a temperature which is at least 10° C. below the reaction temperature.

The first reaction stage and, if appropriate, the at least one further reaction stage may be designed as a bubble column, airlift reactor, stirred tank, propeller loop reactor, jet loop reactor or a combination of these reactor types. The first reaction stage and, if appropriate, the at least one further reaction stage are preferably designed in the form of jet loop reactors. This has the advantage that good mass transfer and complete backmixing within the reaction stages is achieved. In a jet loop reactor, a portion of the reaction mixture is withdrawn from the reaction stage and fed back to the reaction stage through a nozzle in the upper region. This generates a ring flow in the reaction stage. The nozzle is preferably arranged axially in the reaction stage. In a preferred embodiment, a guide tube which is flowed around by the reaction mixture is present in the reactor. In this case, the guide tube extends essentially over the entire length of the reactor with the exception of the reactor ends. In addition, the guide tube has a cross-sectional area which is within the range from $1/10$ up to half of the cross-sectional area of the reactor. In a preferred embodiment, the nozzle is arranged above the upper end of the guide tube, preferably spaced apart by from $1/8$ of the diameter of the guide tube up to one diameter of the guide tube. It is also possible in a particularly preferred embodiment that the nozzle is immersed into the guide tube in a depth up to several diameters of the guide tube.

The reaction mixture added via the nozzle and the gas thus flow through the guide tube first. After flowing through the guide tube, the mixture either impinges on the reactor bottom or preferably on an impingement plate which is arranged between the lower end of the guide tube and the reactor bottom. This deflects the reaction mixture, which flows through a space surrounding the guide tube back in the opposite direction. This generates a ring flow.

The heat which arises in the reaction is generally removed from the reaction mixture by means of a heat exchanger. The heat exchanger may be arranged either within the reactor or outside the reactor. When the heat exchanger is arranged within the reactor, it is preferred when, for example, heat exchanger tubes are arranged in the ring space between the guide tube and the outer wall of the reactor. Alternatively, however, it is also possible that, for example, heat exchanger tubes are arranged in the interior of the guide tube or that heat exchanger tubes are arranged both in the guide tube and in the ring space which surrounds the guide tube. Instead of heat exchanger tubes, it is also possible to use any other form of heat exchanger elements which can be positioned within the reactor. Moreover, it is also possible that the reactor is, for example, temperature-controlled at the outer wall. For this purpose, it is possible, for example, that the reactor is provided with a jacket through which a heat carrier can flow. A further possibility is also that the guide tube is designed as a tube coil and is flowed through by a heat carrier, which controls the temperature of the reaction zone.

When the heat exchanger is arranged outside the reactor, it is preferably arranged in such a way that the proportion of the reaction mixture which is withdrawn from the reactor and is fed back to the reactor via the nozzle in the upper region is passed through the heat exchanger and thus temperature-controlled.

In the case of use of an external heat exchanger which is arranged in the liquid circulation, any heat exchanger known to those skilled in the art can be used. For example, it is possible to use tube bundle heat exchangers, plate heat exchangers, spiral heat exchangers.

The nozzle with which the reaction mixture is fed to the jet loop reactor is preferably a two-substance nozzle. This two-substance nozzle is also used, together with the reaction mixture, to supply the oxygen required for the reaction in the form of the oxygenous gas stream. The use of the two-substance nozzle gives rise to mixing of the reaction mixture with the oxygenous gas, the oxygenous gas being entrained with the flow. Good mass transfer of oxygen into the liquid and homogeneous distribution of the oxygenous gas in the reaction mixture is achieved. This achieves the effect that the organic compound is converted uniformly in the reactor.

The reactors of the first and, if appropriate, of the at least one further reaction stage, i.e. the reactors of all reaction stages apart from the adiabatically operated reaction stage, may have the same or different reactor volume. All reactors preferably have the same reaction volume.

Preference is given to connecting all reactors in series, but it is also possible that the reactors of the individual reaction stages are each designed as two parallel apparatuses.

In addition to the embodiment in which the nozzle of the jet loop reactors is arranged at the upper end of the guide tube, it is also possible that the nozzle is arranged at the lower end of the guide tube. This leads to flow of the reaction medium in the guide tube from the bottom upward and, in the ring space around the guide tube, from the top downward. However, preference is given to the embodiment in which the nozzle is arranged in the upper part of the guide tube and the reaction mixture in the guide tube flows from the top downward. It is the advantage of this embodiment that the gas bubbles have to travel a longer route before they flow into the downstream reaction zone and thus have a higher mean residence time. As a result of this higher residence time of the gas, the achievable conversion and hence the oxygen depletion in the gas bubbles required for the safety of the reaction system before they leave the liquid surface is higher with the nozzle pointed downward than with the nozzle pointed upward.

The organic substance to be oxidized is preferably fed to the liquid circulation system of the first reactor. More preferably, the organic substance is supplied to the circulation pump on the pressure side. In the case of a plurality of reaction stages upstream of the adiabatically operated reaction stage, it is possible that a portion of the organic substance is supplied to the liquid circulation system of the first reactor, and further portions to the liquid circulation systems of the further reactors. In this context, it is possible that a portion of the organic substance is fed to each reactor, or it is possible that the organic substance is supplied only to some of the reaction stages. However, it is preferred that the organic substance which is to be oxidized is supplied only to the first reaction stage.

The liquid effluent from the first and, if appropriate, the at least one further reaction stage, i.e. from the reactors of all reaction stages apart from the adiabatically operated reaction stage, is withdrawn at a suitable point. Suitable points are those at which only a small amount of gas is still present in the liquid. It is, for example, possible to withdraw the liquid effluent at the upper end of the reactors by means of a weir with an overflow. It is likewise possible to withdraw the liquid effluent at the lower end of the reactor below the impingement plate. It is also conceivable to withdraw the liquid effluent from the external circulation system. Particular preference is given to withdrawal of the liquid effluent from the external circulation system and there more preferably on the pressure side of the circulation pump, but upstream of the feed side for the substance to be oxidized.

The adiabatically operated reaction stage can be operated either in monophasic liquid form or sparged with oxygenous gas. The reactor type with monophasic liquid flow used may, for example, be a tubular reactor, a column cascaded with sieve trays or a column with random packing. The reactor type with biphasic gaseous and liquid flow used may, for example, be a tubular reactor, a bubble column, a bubble column cascaded with sieve trays, a column with random packing or a jet loop reactor. The adiabatically operated reaction stage is preferably not backmixed and is designed in the form of a column compartmented with sieve trays or of a compartmented bubble column.

The reaction mixture which enters the adiabatically operated reaction zone comprises, in one embodiment, unconverted oxygen from the preceding reaction stage dissolved in the liquid. When the adiabatically operated reaction stage is additionally sparged with oxygenous gas, the oxygen ascends in the reaction mixture in the form of bubbles. The reaction mixture is mixed by the ascending bubbles. As a result of this, the reaction mixture has contact with the oxygen, and remaining organic compounds are oxidized with the oxygen. As a result of the adiabatic and backmixing-free mode of operation, the temperature of the liquid phase increases over the length of the adiabatic reaction stage. Since the reaction rate of oxidations generally increases with higher temperature, this ensures virtually full conversion of the reactant to be oxidized by the time it leaves the reactor.

In a preferred embodiment, oxygenous gas is supplied to the adiabatically operated reaction stage. The oxygenous gas which is supplied to the adiabatic reaction stage is preferably the same as that which has been supplied to the preceding reaction stages.

In a particularly preferred embodiment, the offgas of the reaction stage preceding the adiabatically operated reaction stage is supplied to the adiabatically operated reaction stage.

When oxygenous gas is supplied to the adiabatically operated reaction stage, either the offgas of the preceding reaction stage or fresh oxygenous gas, this can be done in cocurrent or countercurrent to the liquid flow. Preference is given to adding the gas in countercurrent. The addition is effected especially when the adiabatically operated reaction stage is designed in the form of a bubble column or in the form of a sparged tubular reactor.

In order to achieve good mass transfer between gas and liquid, and in spite of this to prevent the backmixing of the liquid phase over the reactor length, internals are preferably present in the adiabatically operated reaction stage designed in the form of a bubble column or in the form of a sparged tubular reactor. The internals are, for example, impingement plates or sieve trays, a structured packing or a bed of random packing. However, the internals are preferably sieve trays.

When the adiabatically operated reaction stage is designed in the form of a bubble column or in the form of a sparged tubular reactor and the gas is supplied in countercurrent, it is preferred when the gas is supplied to the adiabatically operated reaction stage from the bottom, and the liquid reaction mixture from the top. In this way, the liquid reaction mixture in the reactor flows from the top downward, while the gas flows from the bottom upward. As a result of this countercurrent method, any lower-boiling reactant is stripped out of the product stream and hence the conversion in the reactor is increased. As a result of the internals present in the preferred embodiment, good mass transfer between gas and liquid is achieved. In addition, backmixing of the liquid phase within the adiabatically operated reaction stage can be suppressed by the internals.

The reaction mixture may, as well as reactant and product, also comprise a solvent. The solvents used are those solvents which are inert under reaction conditions. Suitable solvents are, for example, water, aliphatic or aromatic, optionally substituted hydrocarbons, esters, ketones, carboxylic acids, ethers, halogenated hydrocarbons or anhydrides of aliphatic carboxylic acids. However, preference is given to performing the reaction without solvent. The advantage of the reaction without solvent is that no solvent has to be removed after the reaction.

The reaction mixture may further comprise homogeneous or suspended heterogeneous catalysts. In the case of the reaction of aldehydes to give their corresponding carboxylic acid, the reaction is preferably performed without the addition of a catalyst. When, however, the aldehyde to be oxidized has a branch in the $\alpha$-position to the aldehyde group, bases can be added to increase the selectivity. Suitable bases are, for example, alkali metal or alkaline earth metal hydroxides, alkali metal or alkaline earth metal hydrogencarbonates or alkali metal or alkaline earth metal carboxylates. Particularly suitable bases are alkali metal hydroxides, alkali metal carbonates, alkali metal hydrogencarbonates or alkali metal carboxylates. Very particularly preferred bases are sodium hydroxide and potassium hydroxide, which may also be used in the form of aqueous solutions.

Embodiments of the invention are shown in the drawings and are described in detail in the description which follows.

Figure 2:
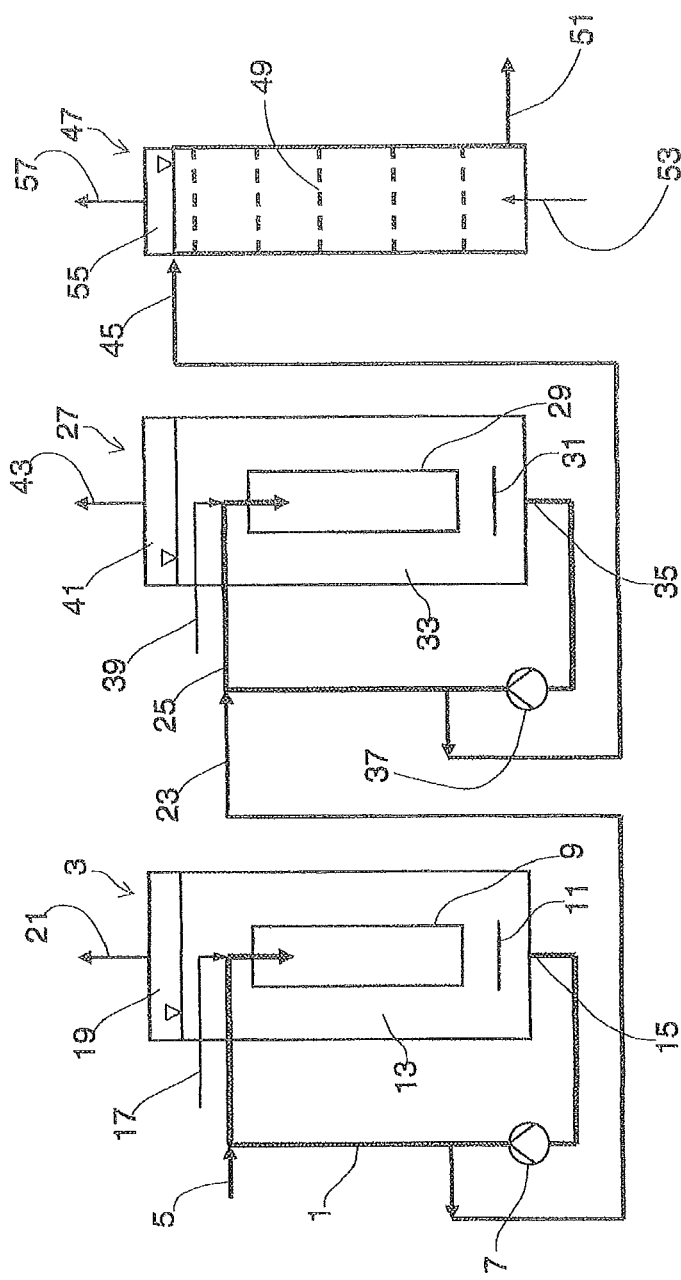
Figure 3:
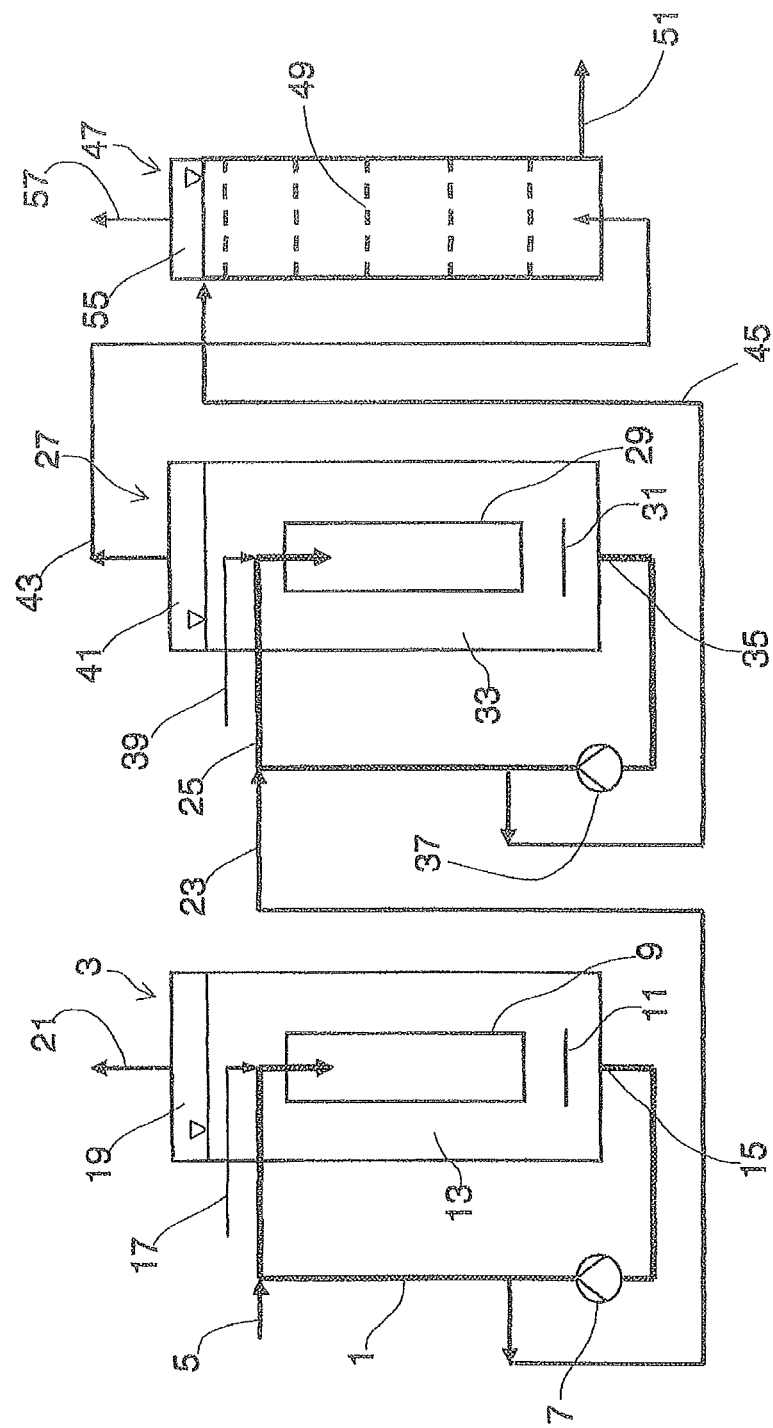

The drawings show:

FIG. 1 a schematic illustration of the process according to the invention in a first embodiment, FIG. 2 a schematic illustration of the process according to the invention in a second embodiment, FIG. 3 a schematic illustration of the process according to the invention in a third embodiment.

FIG. 1 shows a schematic illustration of the process according to the invention in a first embodiment.

Liquid reactant is added to a liquid circulation system 1 of a first reactor 3 via a reactant feed 5. According to the invention, the liquid reactant is an organic substance, preferably an aldehyde. In order that the liquid circulates in the liquid circulation system 1, it is equipped with a pump 7.

The liquid from the liquid circulation system 1 is fed to the first reactor 3 via a nozzle. The first reactor 3 is designed in the form of a jet loop reactor. A guide tube 9 is accommodated in the first reactor 3. The liquid is fed in in the upper part of the guide tube 9. As a result of this, a flow directed downward forms in the guide tube 9. This flows against an impingement plate 11 at which the flow is deflected, such that it can flow upward again in a ring space 13 which surrounds the guide tube 9. It is also possible to dispense with the impingement plate 11, in which case the liquid flows through the guide tube 9 down to the bottom of the first reactor 3 and is deflected at the bottom. At the bottom of the first reactor 3 is arranged a liquid withdrawal 15, through which a portion of the liquid is fed to the liquid circulation system 1.

The nozzle through which the liquid from the liquid circulation system 1 is added to the first reactor 3 is preferably a two-substance nozzle. This nozzle is used to supply the oxygenous gas required for the reaction in the first reactor 3. For this purpose, the two-substance nozzle is equipped with a gas supply 17. The gas supply 17 is used to supply oxygenous gas to the first reactor 3. According to the invention, the oxygenous gas has an oxygen content of less than 50% by volume. The oxygenous gas which is supplied via the gas supply 17 is preferably air.

As a result of the supply of liquid and gas through the two-substance nozzle, intimate mixing of liquid and gas takes place in the first reactor 3.

In the ring space 13, the gas bubbles present in the liquid ascend. They are separated at least partly from the liquid, such that a gas space 19 forms in the first reactor 3 above the liquid. The gas collected in the gas space 19 is withdrawn from the first reactor 3 via an offgas line 21.

A liquid withdrawal 23 is used to withdraw liquid from the pumped circulation system of the first reactor 3. This is fed to a liquid circulation system 25 of a second reactor 27. The second reactor 27 is designed as a jet loop reactor analogously to the first reactor 3. The liquid from the liquid circulation system 25 is supplied to the second reactor 27 via a nozzle. A guide tube 29 is present in the second reactor 27. The liquid from the liquid circulation system 25 is added in the upper region of the guide tube 29, such that a liquid flow from the top downward is generated in the guide tube 29. The liquid flows against an impingement plate 31, at which it is deflected, such that the liquid flows upward in a ring space 33 which surrounds the guide tube 29. As in the first reactor 3 too, it is possible to dispense with the impingement plate 31 in the second reactor 27.

In this case, the liquid is deflected at the bottom of the reactor 27. At the bottom of the second reactor 27, a liquid withdrawal 35 is incorporated. At the liquid withdrawal 35, liquid for the liquid circulation system 25 is withdrawn. The flow in the liquid circulation system 25 is generated by a pump 37.

The nozzle through which the liquid from the liquid circulation system 25 is fed to the second reactor 27 is, just like in the first reactor 3, preferably a two-substance nozzle. The two-substance nozzle likewise feeds a gas stream to the second reactor 27. To this end, the two-substance nozzle is connected to a second gas feed 39. The second gas feed 39 is used to supply an oxygenous gas stream to the second reactor 27. Just like the gas stream fed to the first reactor 3, the oxygenous gas stream comprises not more than 50% by volume of oxygen. The gas stream supplied via the second gas feed 39 is more preferably air.

Since the second reactor 27, just like the first reactor 3, is designed as a jet loop reactor and functions in a similar way, a gas space 41 forms above the liquid in the second reactor 27 too. Gas which separates out from the liquid collects in the gas space 41. The gas is withdrawn from the gas space 41 by means of a second offgas line 43.

The liquid from the second reactor 27 is preferably withdrawn from the pumped circulation system of the second reactor 27. For this purpose, a liquid withdrawal 45 is provided. The liquid withdrawn still comprises oxygen dissolved therein. The liquid withdrawal 45 is used to supply the liquid to a third reactor 47, in which the oxygen dissolved in the liquid reacts adiabatically. The third reactor 47 is preferably designed as a compartmented column. The liquid flow is preferably from the top downward. Suitable and preferred internals for cascading are, for example, sieve trays 49. Alternatively, the internals used may also be impingement plates, structured packings or beds of random packings.

A product withdrawal 51 is used to withdraw the product prepared. The product can, for example, be fed to a downstream workup in order to remove any reactant still present in the product stream. In addition, the workup may, if appropriate, also have a gas separator in order to remove gas still present in the product stream.

The offgas withdrawn via offgas lines 21 and 43 is, for example, disposed of. However, it is preferred that the offgas withdrawn via offgas lines 21 and 43 is worked up in order to recover any product and reactant present in the offgas. The reactant can then be sent back to the reaction. Reactant and product are removed from the offgas preferably by scrubbing in a scrubbing column. In this case, any desired scrubbing column known to those skilled in the art can be used. Suitable scrubbing liquids are, for example, water, any solvent used or the product. More preferably, the scrubbing liquid used is the product which is being produced in the plant at the time. Most preferably, the scrubbing substance used is the liquid product from the adiabatically operated reaction stage. In a particularly preferred embodiment, the scrubbing substance used is cooled before use to a temperature which is at least 10° C. below the reaction temperature.

FIG. 2 shows a schematic illustration of a second embodiment of the process according to the invention.

The embodiment shown in FIG. 2 differs from the embodiment shown in FIG. 1 in that the third reactor 47 is sparged. To this end, an oxygenous gas stream is supplied to the adiabatic reactor 47 via a third gas feed 53. The oxygenous gas stream preferably has the same composition as that which is fed to the first reactor 3 via the first gas feed 17 and that which is fed to the second reactor 27 via the second gas feed 39. In the adiabatic reactor 47, which is preferably designed as a bubble column, the gas which has been added via the third gas feed 53 ascends. Since the liquid from the second reactor 47 is added at the top to the adiabatic reactor 47 via the liquid withdrawal 45 and thus flows from the top downward, gas and liquid flow in countercurrent in the adiabatic reactor 47. Uniform gas distribution in the adiabatic reactor 47 is achieved by virtue of the internals, preferably the sieve trays 49. Once the gas has flowed through the liquid, it separates out from the liquid and is collected in a gas space 55. The gas is withdrawn from the adiabatic reactor 47 through an offgas line 57.

The offgas withdrawn via offgas lines 21, 43 and 57 is treated analogously to the embodiment according to FIG. 1.

FIG. 3 shows a schematic illustration of the process according to the invention in a third embodiment. The embodiment shown in FIG. 3 differs from the embodiment shown in FIG. 2 in that the offgas from the reactor 27 is fed to the adiabatic reactor 47. This has the advantage that oxygen still present in the offgas of the second reactor 27 can be converted in the adiabatic reactor 47, and in this way the amount of offgas is reduced compared to the embodiment in FIG. 2. At the same time, the amount of oxygenous gas required is also lower than in the embodiment shown in FIG. 2. In order to sparge the adiabatic reactor 47 with the offgas of the second reactor 27, the second offgas line 43 of the second reactor 27 opens out at the bottom of the adiabatic reactor 47. Here, the gas is supplied via a customary gas distributor known to those skilled in the art. The offgas of the second reactor 27 ascends in the adiabatic reactor 47. Since, just like in FIG. 2, the liquid is added to the adiabatic reactor 47 at the top, liquid and gas in the adiabatic reactor 47 flow in countercurrent. Once the gas has flowed through the liquid, it is collected in the gas space 55 and disposed of via the offgas line 57.

The offgas withdrawn via the offgas lines 21 and 57 is treated analogously to the embodiment according to FIG. 1.

The first reactor 3 and the second reactor 27 are preferably operated isothermally. To this end, it is necessary, in the case of an exothermic reaction, to remove the heat which arises. For heat removal from the first reactor 3 and the second reactor 27, heat exchangers are typically used. The heat exchanger may be arranged either in the liquid circulation system 1, 25 or else preferably in the first reactor 3 or second reactor 27. When the heat exchanger is arranged in the reactor 3, 27, it is possible firstly that the heat exchanger is arranged in the interior of the particular guide tube 9, 29 or, alternatively and preferably, in the ring space 13, 33 which surrounds the guide tube 9, 29. It is also possible that the heat exchanger is arranged both within the guide tube 9, 29 and in the ring space 13, 33.

The heat exchanger used may be any desired heat exchanger known to those skilled in the art. In a preferred embodiment, however, heat exchange tubes are used. In particular, it is preferred that the heat exchange tubes are arranged in the ring space 13, 33 which surrounds the particular guide tube 9, 29 of the first reactor 3 or of the second reactor 27.

In addition to the embodiment shown in FIGS. 1 to 3 with a first reactor 3 and a second reactor 27, each of which is designed as a loop reactor, it is also possible that only two reactors are used for the reaction. In this case, the second reactor 27 is dispensed with. However, it is also possible that more than two isothermally operated reactors 3, 27 are used. These are connected downstream of and in series with the two reactors 3, 27 shown, and upstream of the adiabatically operated, reactor 47. The construction and the connection of the additional reactors correspond to those of the first reactor 3 and of the second reactor 27.

EXAMPLES

Examples 1 to 3

In a plant composed of two jet loop reactors connected in series and an unsparged adiabatic tubular reactor connected downstream, propionaldehyde was oxidized with air to propionic acid. The jet loop reactors were each of the same design. The reactor shell had a diameter of 1.5 m and a height of 9.5 m. The effective reaction volume was 12 m$^3$. In each case, an inner tube with a diameter of 0.5 m is mounted in an axially centered manner in the jet loop reactors, which serves as a guide tube. Below the inner tube is mounted an impingement plate which deflects the flow. Below the impingement plate, the liquid is sucked out of the reactor and conducted back into the reactor by means of a pump via an axially centered two-substance nozzle mounted close to the upper end of the inner tube. The fresh aldehyde was added on the pressure side of the pump. The two-substance nozzle was likewise used to feed in air used as the oxidation gas. The heat of reaction is removed via heat exchange tubes which are mounted in the annulus between reactor wall and inner tube and are cooled with cooling water, and the temperature is at the same time kept substantially constant. In the upper part of the reactor, a calming zone serves to separate liquid and gas. The gas was supplied as offgas to a collecting line. The liquid effluent from the first jet loop reactor, which is withdrawn on the pressure side of the circulation pump but upstream of the aldehyde feed, was used as feed for the second reactor and in turn added on the pressure side of the pump of the liquid circulation system of the second reactor. The supply of the liquid into the second reactor was likewise via a two-substance nozzle, through which additional air was also metered in.

The gas spaces of the jet loop reactors are equipped with online oxygen meters which stop the reaction as soon as the oxygen concentration rises above 10% by volume.

The liquid effluent from the second jet loop reactor was used as feed for an adiabatic tubular reactor which serves as a postreactor. This reactor has a length of 8.5 m and a diameter of 1.5 m and is equipped with four sieve trays. The effective reaction volume is 12 m$^3$.

At the start, all reactors were filled with propionic acid and brought to reaction temperature. Subsequently, the metered addition of propionaldehyde and air was commenced. The liquid effluent was withdrawn under level control and the offgas under pressure control. On attainment of a steady state, i.e. after at least 10 residence times, samples are taken and analyzed.

Tables 1 to 3 summarize the experimental results.

TABLE 1

| | First jet loop reactor | | | | | | |
|---|---|---|---|---|---|---|---|
| | Feeds | | | | Pumped | Aldehyde | O$_2$ content in |
| Example | Aldehyde kg/h | Air kg/h | Temp. °C. | Pressure bar | circulation rate kg/h | conversion % | the offgas % by vol. |
| 1 | 2064 | 2351 | 78 | 19 | 150 | 94.0 | 0.6 |
| 2 | 3166 | 3524 | 74 | 23 | 150 | 91.4 | 0.7 |
| 3 | 4197 | 4707 | 73 | 22 | 150 | 90.5 | 1.2 |

TABLE 2

Second jet loop reactor

| Example | Air feed kg/h | Temp. °C | Pressure bar | Pumped circulation rate kg/h | Aldehyde conversion % | O$_2$ content in the offgas % by vol. |
|---|---|---|---|---|---|---|
| 1 | 142 | 79 | 19 | 101 | 99.0 | 3.1 |
| 2 | 256 | 82 | 23 | 101 | 98.7 | 3.0 |
| 3 | 390 | 83 | 22 | 101 | 98.6 | 3.8 |

TABLE 3

Adiabatic tubular reactor

| Example | Input temp. °C | Output temp. °C | Pressure bar | Aldehyde conversion % | Selectivity for acid % |
|---|---|---|---|---|---|
| 1 | 79 | 82 | 19 | 99.1 | 99.2 |
| 2 | 82 | 86 | 23 | 98.9 | 99.3 |
| 3 | 83 | 87 | 22 | 98.8 | 99.3 |

The by-products identified and analyzed quantitatively in the crude propionic acid or in the offgas were ethyl formate, ethyl propionate, ethanol, acetic acid, formic acid, 2-methyl-pentanoic acid, water, ethane, ethylene, CO$_2$, CO, methane and H$_2$. Other, unidentified secondary components, especially high boilers, were quantified only by GC area % (FID detector).

Examples 1 to 3 show that, even in the case of essentially the same temperature in the reactors and reaction temperatures of above 50° C., high conversions and selectivities can be achieved. In addition, it is found from all three examples that, even in relation to the sum of the effective reaction volumes of 3×12 m$^3$, high space-time yields can be achieved and hence particularly economically viable processes can be configured, since smaller and less expensive reactors can be used for a given production rate. The space-time yields were found to be 71 g/l/h for example 1, 109 g/l/h for example 2 and 144 g/l/h for example 3.

Examples 4 and 5

Examples 4 and 5 differ from examples 1 to 3 in that the adiabatic tubular reactor is replaced by an adiabatic bubble column. The bubble column has a length of 8.5 m and a diameter of 1.5 m and is provided with four sieve trays in order to improve the gas/liquid exchange. The effective reaction volume of the bubble column is 12 m$^2$.

The liquid effluent of the second jet loop reactor is added at the upper end of the bubble column and withdrawn under level control at the lower end. Air is metered into the bubble column from the bottom. The offgas is withdrawn under pressure control at the upper end of the bubble column.

Data of examples 4 and 5 are shown in the tables which follow.

TABLE 4

First jet loop reactor

| Example | Feeds Aldehyde kg/h | Feeds Air kg/h | Temp. °C | Pressure bar | Pumped circulation rate kg/h | Aldehyde conversion % | O$_2$ content in the offgas % by vol. |
|---|---|---|---|---|---|---|---|
| 4 | 4733 | 5231 | 73 | 22 | 150 | 89.8 | 1.2 |
| 5 | 5364 | 5845 | 73 | 22 | 150 | 88.8 | 1.2 |

TABLE 5

Second jet loop reactor

| Example | Air feed kg/h | Temp. °C | Pressure bar | Pumped circulation rate kg/h | Aldehyde conversion % | O$_2$ content in the offgas % by vol. |
|---|---|---|---|---|---|---|
| 4 | 527 | 83 | 22 | 101 | 98.1 | 3.5 |
| 5 | 654 | 83 | 22 | 101 | 97.9 | 3.5 |

TABLE 6

Adiabatic bubble column with fresh air sparging

| Example | Air feed kg/h | Input temp. °C | Output temp. °C | Pressure bar | O$_2$ content in the offgas % by vol. | Aldehyde conversion % | Selectivity for acid % |
|---|---|---|---|---|---|---|---|
| 4 | 130 | 83 | 110 | 22 | 3.8 | 99.9 | 99.8 |
| 5 | 160 | 83 | 113 | 22 | 4.2 | 99.9 | 99.8 |

As these examples demonstrate, it is possible to achieve virtually complete aldehyde conversions with very good selectivities in continuous operation, without any need to keep reaction temperatures below 50° C. With a low level of additional complexity for the sparging in the adiabatic reactor, it is possible to further increase the space-time yields and the aldehyde conversions compared to examples 1 to 3. The space-time yields are found to be 163 g/l/h for example 4 and 188 g/l/h for example 5.

Examples 6 and 7

In these examples, in contrast to examples 4 and 5, the bubble column is sparged with the offgas of the second jet loop reactor.

The tables show the data for examples 6 and 7.

TABLE 7

| | First jet loop reactor | | | | | | |
|---|---|---|---|---|---|---|---|
| | Feeds | | | | Pumped | Aldehyde | $O_2$ content in |
| Example | Aldehyde kg/h | Air kg/h | Temp. °C. | Pressure bar | circulation rate kg/h | conversion % | the offgas % by vol. |
| 6 | 4733 | 5231 | 73 | 22 | 150 | 89.8 | 1.2 |
| 7 | 5364 | 5845 | 73 | 22 | 150 | 88.8 | 1.2 |

TABLE 8

| | Second jet loop reactor | | | | | |
|---|---|---|---|---|---|---|
| Example | Air feed kg/h | Temp. °C. | Pressure bar | Pumped circulation rate kg/h | Aldehyde conversion % | $O_2$ content in the offgas % by vol. |
| 6 | 527 | 83 | 22 | 101 | 98.1 | 3.5 |
| 7 | 654 | 83 | 22 | 101 | 97.9 | 3.5 |

TABLE 9

| | Adiabatic bubble column, sparging with the offgas of the second reactor | | | | |
|---|---|---|---|---|---|
| Example | Input temp. °C. | Output temp. °C. | Pressure bar | $O_2$ content in the offgas % by vol. | Aldehyde conversion % |
| 6 | 83 | 105 | 22 | 0.19 | 99.5 |
| 7 | 83 | 107 | 22 | 0.35 | 99.5 |

It is found that the conversions in the case of sparging of the bubble column with the offgas of the second reactor are somewhat lower than the conversions in the case of sparging of the bubble column with air. However, an advantage is that additional fresh air metering and online oxygen monitoring can be dispensed with. In addition, the amount of offgas is comparable to the amount of offgas of examples 1 to 3 and lower than in examples 4 and 5.

The space-time yields are 163 g/l/h for example 6 and 188 g/l/h for example 7.

Example 8

Oxidation of n-valeraldehyde with Air

Example 2 is repeated, except that n-valeraldehyde is used as a feedstock instead of propionaldehyde. The results are compiled in the tables which follow.

TABLE 10

| | First jet loop reactor | | | | | | |
|---|---|---|---|---|---|---|---|
| | Feeds | | | | Pumped | Aldehyde | $O_2$ content in |
| Example | Aldehyde kg/h | Air kg/h | Temp. °C. | Pressure bar | circulation rate m³/h | Conversion % | the offgas % by vol. |
| 8 | 3166 | 2524 | 74 | 23 | 150 | 94.3 | 0.6 |

TABLE 11

| | Second jet loop reactor | | | | | |
|---|---|---|---|---|---|---|
| Example | Air feed kg/h | Temp. °C. | Pressure bar | Pumped circulation rate m³/h | Aldehyde conversion % | $O_2$ content in the offgas % by vol. |
| 8 | 146 | 82 | 23 | 101 | 99.5 | 3.1 |

TABLE 12

Adiabatic tubular reactor

| Example | Input temp. °C. | Output temp. °C. | Pressure bar | Aldehyde conversion % |
|---|---|---|---|---|
| 8 | 82 | 86 | 23 | 99.8 |

Example 9

Oxidation of 3,5,5-trimethylhexanal with Air

Example 2 is repeated, except that 3,5,5-trimethylhexanal is used as a feedstock instead of propionaldehyde. The results are compiled in the tables which follow.

TABLE 13

First jet loop reactor

| Example | Feeds Aldehyde kg/h | Air kg/h | Temp. °C. | Pressure bar | Pumped circulation rate m³/h | Aldehyde conversion % | $O_2$ content in the offgas % by vol. |
|---|---|---|---|---|---|---|---|
| 9 | 3166 | 1600 | 74 | 23 | 150 | 97.5 | 0.6 |

TABLE 14

Second jet loop reactor

| Example | Air feed kg/h | Temp. °C. | Pressure bar | Pumped circulation rate m³/h | Aldehyde conversion % | $O_2$ content in the offgas % by vol. |
|---|---|---|---|---|---|---|
| 9 | 40 | 82 | 23 | 101 | 99.8 | 3.1 |

TABLE 15

Adiabatic tubular reactor

| Example | Input temp. °C. | Output temp. C. | Pressure bar | Aldehyde conversion % |
|---|---|---|---|---|
| 9 | 82 | 83 | 23 | 99.9 |

Comparative Example 1

Oxidation of Propionaldehyde with Air

Comparative example 1 is performed analogously to example 1, except that, based on the teaching of WO 01/66505, a temperature of 50° C. is established in the first jet loop reactor, and a temperature of 70° C. in the second jet loop reactor. The input temperature to the adiabatic tubular reactor is likewise 70° C.

TABLE 16

First jet loop reactor

| Comparative example | Feeds Aldehyde kg/h | Air kg/h | Temp. °C. | Pressure bar | Pumped circulation rate m³/h | Aldehyde conversion % | $O_2$ content in the offgas % by vol. |
|---|---|---|---|---|---|---|---|
| 1 | 2064 | 2200 | 50 | 19 | 150 | 87.4 | 0.6 |

TABLE 17

Second jet loop reactor

| Comparative example | Air feed kg/h | Temp. °C. | Pressure bar | Pumped circulation rate m³/h | Aldehyde conversion % | $O_2$ content in the offgas % by vol. |
|---|---|---|---|---|---|---|
| 1 | 344 | 70 | 19 | 101 | 98.1 | 3.1 |

TABLE 18

| | Adiabatic tubular reactor | | | |
|---|---|---|---|---|
| Comparative example | Input temp. °C. | Output temp. °C. | Pressure bar | Aldehyde conversion % |
| 1 | 70 | 74 | 19 | 98.3 |

Compared to example 1, a significantly lower conversion of propionaldehyde is found according to the teaching of WO 01/66505.

| List of reference numerals | |
|---|---|
| 1 | Liquid circulation system |
| 3 | First reactor |
| 5 | Reactant feed |
| 7 | Pump |
| 9 | Guide tube |
| 11 | Impingement plate |
| 13 | Ring space |
| 15 | Liquid withdrawal |
| 17 | Gas feed |
| 19 | Gas space |
| 21 | Offgas line |
| 23 | Liquid withdrawal |
| 25 | Liquid circulation system |
| 27 | Second reactor |
| 29 | Guide tube |
| 31 | Impingement plate |
| 33 | Ring space |
| 35 | Liquid withdrawal |
| 37 | Pump |
| 39 | Second gas feed |
| 41 | Gas space |
| 43 | Second offgas line |
| 45 | Liquid withdrawal |
| 47 | Adiabatic reactor |
| 49 | Sieve trays |
| 51 | Product withdrawal |
| 53 | Third gas feed |
| 55 | Gas space |
| 57 | Offgas line |

The invention of claimed is:

1. A process for oxidizing at least one aldehyde with oxygen, which comprises the following steps:
   (a) adding the at least one aldehyde as a liquid and an oxygenous gas stream to a first reaction stage to form a reaction mixture, at least some of the oxygen reacting with the organic compound to form a reaction product,
   (b) adding the reaction mixture from the first reaction stage to an adiabatically operated reaction stage in which the unconverted aldehyde reacts further at least partly to give the product,
   wherein the reaction mixture from the first reaction stage, before being added to the adiabatically operated reaction stage, is sent to at least one further reaction stage, and
   wherein the first reaction stage and the at least further reaction stage are operated at essentially the same temperature, or are operated such that the temperature increases from reaction stage to reaction stage, and wherein oxygenous gas is supplied to the at least one further reaction stage.

2. The process according to claim 1, wherein the first reaction stage and the at least one further reaction stage are operated essentially isothermally.

3. The process according to claim 1, wherein oxygenous gas is supplied to the adiabatically operated reaction stage.

4. The process according to claim 1, wherein offgas of at least one of the preceding reaction stages is supplied to the adiabatically operated reaction stage.

5. The process according to claim 1, wherein the first reaction stage and the at least one further reaction stage are designed in the form of jet loop reactors.

6. The process according to claim 1, wherein the adiabatically operated reaction stage is designed in the form of a bubble column, of a jet loop reactor or of a sparged tubular reactor.

7. The process according to claim 6, wherein the gas supplied to the adiabatically operated reaction stage designed in the form of a bubble column or in the form of a sparged tubular reactor is added in countercurrent.

8. The process according to claim 6, wherein the adiabatically operated reaction stage designed in the form of a bubble column or in the form of a sparged tubular reactor comprises internals.

9. The process according to claim 8, wherein the internals are impingement plates or sieve trays, or a structured packing, or a bed of random packing.

10. The process according to claim 1, wherein the organic substance which is added to the first reaction stage is an aldehyde which is oxidized to its corresponding acid.

11. The process according to claim 10, wherein the aldehyde is an aldehyde having from 3 to 18 carbon atoms.

12. The process according to claim 10, wherein the aldehyde is saturated.

13. The process according to claim 11, wherein the aldehyde is saturated.

14. The process according to claim 10, wherein the aldehyde is selected from propanal, butanal, 2-methylpropanal, pentanal, 2-methylbutanal, 3-methylbutanal, 2,2-dimethylpropanal, hexanal, 2-methylpentanal, 3-methylpentanal, 2-ethylbutanal, heptanal, 2-methylhexanal, 2-ethylpentanal, octanal, 2-ethylhexanal, nonanal, decanal, 3,7-dimethyloctanal, 3,5,5-trimethylhexanal, cyclopentanecarbaldehyde, cyclohexanecarbaldehyde or a mixture of at least two of the aforementioned aldehydes.

15. The process according to claim 1, wherein the proportion of oxygen in the oxygenous gas stream is less than 50% by volume.

16. The process according to claim 1, wherein the oxygenous gas stream is air.

17. The process according to claim 1, wherein unconverted organic substance and product present in the offgas obtained in the reaction are removed therefrom and the unconverted organic substance is sent back to the reaction.

18. The process according to claim 17, wherein the organic substance and the product are removed from the offgas by scrubbing in a scrubbing column.

19. The process according to claim 6, wherein the adiabatically operated reaction stage is designed in the form of a bubble column.

20. The process according to claim 9, wherein the internals are sieve trays.

* * * * *